US007749728B2

(12) United States Patent
Minchinton et al.

(10) Patent No.: US 7,749,728 B2
(45) Date of Patent: Jul. 6, 2010

(54) METHOD AND SYSTEM FOR MEASURING THE PENETRATION OF DRUGS AND OTHER SUBSTANCES INTO TISSUE

(75) Inventors: Andrew I. Minchinton, Vancouver (CA); Alastair H. Kyle, Vancouver (CA)

(73) Assignee: Cabenda Pharmaceutical Research Limited

(*) Notice: Subject to any disclaimer, the term of this patent is extended or adjusted under 35 U.S.C. 154(b) by 584 days.

(21) Appl. No.: 10/559,320

(22) PCT Filed: Jun. 4, 2004

(86) PCT No.: PCT/CA2004/000836

§ 371 (c)(1), (2), (4) Date: Jun. 8, 2006

(87) PCT Pub. No.: WO2004/113477

PCT Pub. Date: Dec. 29, 2004

(65) Prior Publication Data

US 2007/0065802 A1    Mar. 22, 2007

Related U.S. Application Data (60) Provisional application No. 60/475,467, filed on Jun. 4, 2003.

(51) Int. Cl.
*C12P 1/00* (2006.01)

(52) U.S. Cl. ........................................................ 435/41

(58) Field of Classification Search ........................ None
See application file for complete search history.

(56) References Cited

U.S. PATENT DOCUMENTS 6,110,208 A    8/2000   Soranzo et al.

FOREIGN PATENT DOCUMENTS

EP    0 590 513 A    4/1994
EP    0 671 469 A    9/1995
WO   WO 97/00314    1/1997

OTHER PUBLICATIONS

Papaioannou et al. "Multi-Layered Periodontal Pocket Epithelium Reconstituted in Vitro: Histology and Cytokeratin Profiles", J of Periodontology, 1999, 70(6):668-678.*
Fusco et al. "Penetration of Schistosoma mansoni Cercariae into a living skin equivalent", J of Parasitology, 1993, 79(3):444-448.*
Tsujihashi et al. "Cell proliferation of human bladder tumors determined by BRDURD and Ki-67 immunostaining", J of Urology, 1991, 145:846-849.*
Kyle et al. "Measurement of delivery and metabolism of tirapazamine to tumour tissue using the multilayered cell culture model", Cancer Chemother Pharmacol 1999, 43:213-220.*
Gumbleton, Mark, et al., "Progress and Limitations in the Use of in Vitro Cell Cultures to Serve as a Permeability Screen for the Blood-Brain Barrier", Journal of Pharmaceutical Sciences, vol. 90, No. 11, Nov. 2001, pp. 1681-1698.
Ampasavate, Chadarat, et al., "Transport and metabolism of opioid peptides across BeWo cells, an in vitro model of the placental barrier", International Journal of Pharmaceutics, vol. 233, No. 1-2, Feb. 21, 2002, pp. 85-98.
Guidry, A.J., et al., "A Bovine Mammary Endothelial/Epithelial Cell Culture Model of the Blood/Mild Barrier", Canadian Journal of Veterinary Research, vol. 62, No. 2, Apr. 1998, pp. 117-121.

* cited by examiner

*Primary Examiner*—Karen Cochrane Carlson
*Assistant Examiner*—Bin Shen
(74) *Attorney, Agent, or Firm*—Oyen Wiggs Green & Mutala LLP

(57) ABSTRACT

The failure of many anticancer drugs to control growth of solid cancers may stem in part from inadequate delivery to tumor regions distant from vasculature. However, extricating the effect of tissue penetration from the many other factors that affect a drug's efficacy in tumors with distance from vasculature is generally not possible. The present invention relates to an effect-based assay which employs a multilayered cell culture (MCC), a tissue-engineered disc grown from tumor cells on a permeable membrane. One side of the culture may be exposed to a drug or other test substance while the other side is temporarily sealed off. Cells adjacent both the exposed side and the sealed side, of the MCC may then be compared since they have similar rates of proliferation and other biochemical properties. For example, the effect of the drug or other test substance may be evaluated by immunohistochemical or other labeling techniques. The invention may be applied to discover drugs that exhibit desirable penetration properties.

20 Claims, 10 Drawing Sheets

|  | Ratio of near to far side drug exposure ||
|  | Effect-based assay | Drug fluorescence |
| --- | --- | --- |
| DOX | ~12 | 11 ± 5 (sd) |
| EPI | ~10 | 12 ± 3 (sd) |
| DAU | ~30 | 50 ± 15 (sd) |
| MIT | >30 | -- |

Figure 12

METHOD AND SYSTEM FOR MEASURING THE PENETRATION OF DRUGS AND OTHER SUBSTANCES INTO TISSUE

REFERENCE TO RELATED APPLICATION

This application is the National Stage (35 Usc Section 371) of International Application No. PCT/CA2004/000836, filed 4 Jun. 2004, which claims the benefit of U.S. provisional patent application Ser. No. 60/475,467 filed 4 Jun. 2003, which is hereby incorporated by reference in its entirety.

TECHNICAL FIELD

This application relates to a method and system for measuring the penetration of drugs and other substances within living tissue.

BACKGROUND

The extent that drugs and other substances can penetrate living tissue is clinically important. For example, there is evidence that poor penetration of some anti-cancer drugs limits their effectiveness. The density of blood vessels in cancer tissue can be significantly lower than non-cancerous tissue (1,2). The increased separation of blood vessels in cancer tissue caused by the proliferation of cancer cells leads to a reduction in the ability of molecules supplied by the blood to reach all cells within a tissue (3,4). Inadequate penetration of drugs or other substances may be a problem in other disease states as well, such as infection (e.g. gangrene). Accordingly, systems have been developed in the past for assessing in vitro the penetration potential of anti-cancer agents and the like (5,6).

The most commonly used method for assessing the penetration of agents into living tissue is the multi-cellular spheroid (5). Multi-cellular spheroids are a conglomeration of up to $10^6$ animal cells, which form spheres of tissue and are grown in a flask in which the media is stirred (spinner culture). Penetration of agents into such multi-cellular spheroids can be assessed by applying the agent for a period of time and then either sectioning the spheroids using a cryotome and examining them microscopically or dissociating them and examining individual cells (7,8).

The use of the spheroid system for measuring penetration is effective, but has several significant limitations. The geometry of the penetration into spheroids is almost inverse of some situations encountered in nature, i.e. in many instances drugs diffuse radially outward from capillaries within tissue, while with spheroids the agent diffuses from the outer or maximum surface area toward the center of the sphere.

There are two main drawbacks to using spheroids to measure penetration of an agent. The first is that the concentration of the agent at different depths of penetration cannot always be determined easily. Usually, after a period of time has lapsed to allow penetration of the test agent, the spheroids are removed from the incubating medium and quickly frozen so they may then be sectioned and evaluated. When the agent is fluorescent it can be microscopically evaluated. If radiolabeled (which is expensive and more difficult), a photographic emulsion is applied and then the section is microscopically evaluated. The agent must bind to the cells to permit a detection method involving the dissociation of cells from the spheroid and analysis using flow cytometry. If the agents are not readily identifiable (i.e. colored, fluorescent or radiolabeled) spheroids cannot be used to directly assess their penetration.

The second drawback to using spheroids is that a gradient of energy status, proliferation and other biological parameters forms inwards from the surface of spheroids, which makes it difficult to assess an agent's penetration based on its effect on cells at different depths within the culture. Generally the cells furthest removed from the site of drug exposure are either quiescent or slowly dividing and will therefore have a reduced sensitivity to many drugs (9).

The present invention is an extension of a system for growing multi-layered cell cultures which is the subject of U.S. Pat. No. 5,602,028 issued Feb. 11, 1997 and is hereby incorporated in its entirety by reference. The '028 patent relates to an apparatus and method for growing multi-layered cell cultures on permeable membranes. Each culture is submerged in a liquid growth medium, which contacts both surfaces thereof. The growth medium is circulated past the culture, such as by continuous stirring of the media, to deliver nutrients and oxygen to the culture. Preferably each cell culture is allowed to grow into a multi-layered, substantially planar cell culture mat on its respective membrane. In one embodiment of the invention the membrane and cell culture mat may be transferred to a partition wall between a pair of side by side chambers each containing a liquid medium. The cell cultures may be used for measuring the rate of penetration of an agent, such as a potential drug, through tissue. The drug or other substance to be tested may be inoculated into one of the chambers and the amount or "flux" of drug or other substance passing into the other of the chambers may be measured over time. Such flux measurements may be used to estimate the rate and degree of penetration of the test drug or other substance.

There are several drawbacks to using measurements of flux through multi-layered cell cultures to measure penetration of a drug or other substance. Flux studies are relatively laborious and time-consuming and are not suited to high throughput automated screening. Moreover, flux data is often difficult to interpret. The need has therefore arisen for a system and method for measuring the penetration of a drug or other substance within a multi-layered cell culture using a biological assay. The assay can be used to predict the penetration of the test substance in living tissue.

SUMMARY OF INVENTION

In accordance with the invention, a method for measuring the penetration of a drug or other substance within a multi-layered cell culture is provided. The method includes the steps of providing a multi-layered cell culture disposed on a permeable support membrane, the cell culture having first and second sides. The multi-layered cell culture is oriented so that it is exposed to the drug or other substance to be tested for a discrete period of time from the first side only, the second side being sealed off. Preferably the cells at symmetric locations within the cell culture between the first and second sides are biochemically similar, for example proliferating at a similar rate. At some point after the discrete period of time, the culture is analyzed to determine the effect of the drug or other substance on cells at different depths into the cultures. For example, the cell culture may be stained immunohistochemically to detect cells that continue to proliferate after exposure to an agent of interest using bromodeoxyuridine (BrdUrd), a thymidine analogue which is incorporated into DNA during the S-phase of the cell cycle. Apparatus and kits for carrying out the method are also described. The method may be used as a means of rapidly screening for putative drugs having desirable tissue penetration characteristics.

BRIEF DESCRIPTION OF DRAWINGS

In drawings which illustrate embodiments of the invention, but which should not be construed as restricting the spirit or scope of the invention in any way.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1A:
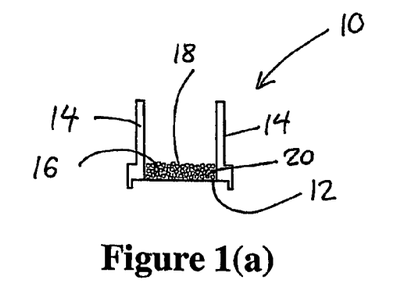
FIG. 1(a) is a cross-section of a cell culture insert containing a multi-layered cell culture (MCC) disposed on a permeable membrane support.
Figure 4:
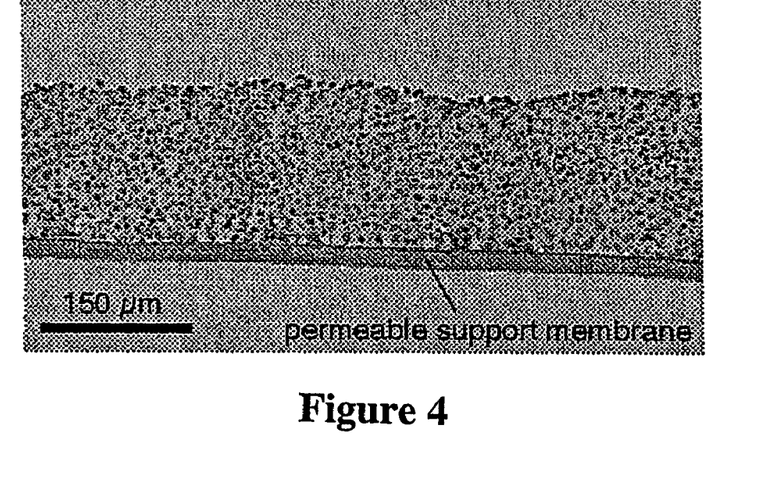
FIG. 4 is a stained section of an 8 day old multi-layered cell culture comprising human cervix cancer cells, the culture having a thickness of approximately 200 μm.

As shown in FIG. 1(a), the present invention may employ a cell culture insert 10 comprising a permeable or semi-permeable membrane 12 held in a cylindrical support 14. A multi-layered cell culture (MCC) 16 having a first side 18 and a second side 20 is grown on membrane 12 as described in U.S. Pat. No. 5,602,028 issued Feb. 11, 1997 which is hereby incorporated by reference. Cell culture 16 may comprise, for example, layers of cells approximately 200 μm in total thickness (FIG. 4). As described in the '028 patent, cell culture 16 is grown while submerged in a liquid growth medium contacting both sides 18, 20 of membrane 12. Accordingly, cells toward both sides 18, 20 of culture 16 are typically proliferating at approximately the same rate. A gradient in cellular proliferation may develop between the exposed sides 18, 20 of culture 16 (which are better supplied with oxygen and nutrients) and a central portion of the culture (where the cells may be primarily non-cycling). The MCC essentially provides a three-dimensional tissue culture model of solid tumors.

Figure 1B:
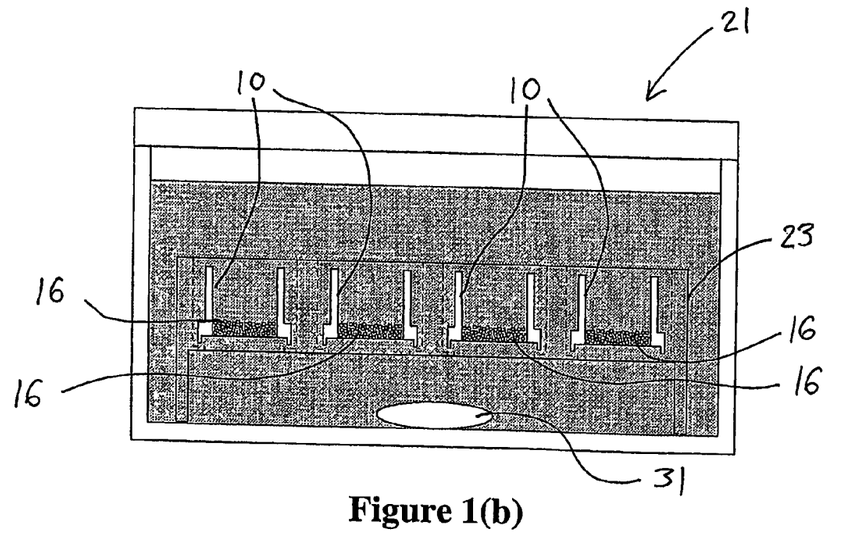
FIG. 1(b) is a diagrammatic representation of a growth vessel used for growing multi-layered cell cultures. The vessel includes a frame designed to maintain multiple cell culture inserts of FIG. 1(a) immersed in stirred media.

FIG. 1(b) illustrates a growth vessel 21 which includes a teflon frame 23 designed to hold multiple MCCs suspended in stirred media. For example, the MCCs may be grown in batches of 8 separate cultures.

Figure 2:
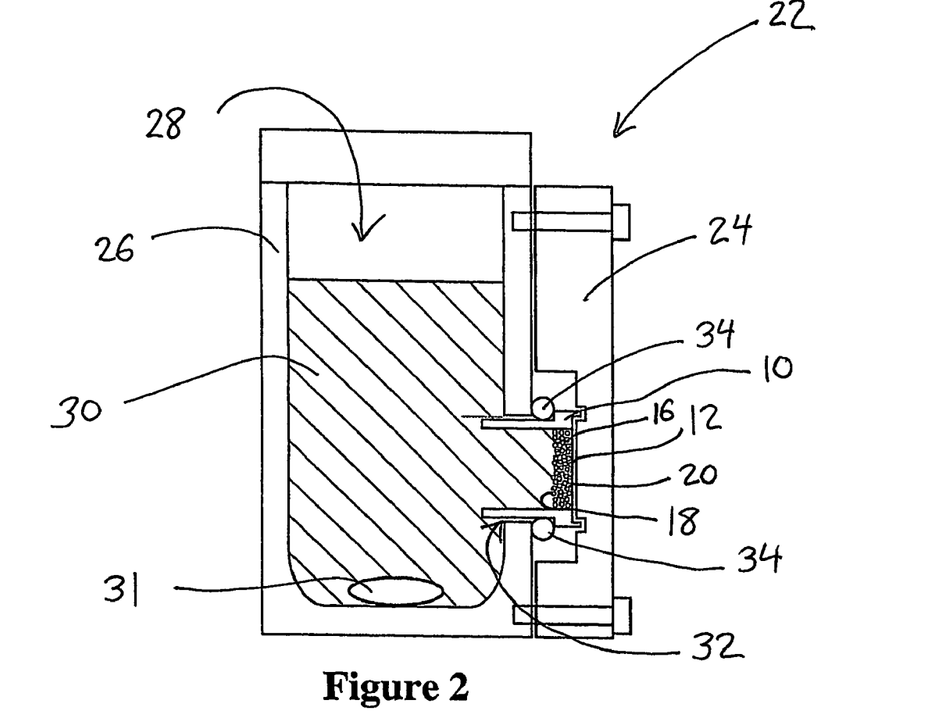
FIG. 2 is a diagrammatic representation of a apparatus for receiving and temporarily supporting an insert of FIG. 1(a) to enable exposure of a test substance to one side thereof.

FIG. 2 depicts an apparatus 22 for receiving and temporarily supporting the cell culture insert 10 of FIG. 1(a). Apparatus 22 includes a back plate 24 coupled to a forward housing 26 defining a reservoir 28. Reservoir 28 contains a liquid growth media 30. A magnetic stir bar 31 is provided within reservoir 28 to stir media 30.

Apparatus 22 allows media 30 to be gassed, stirred and maintained at optimal temperature and permits samples to be taken from reservoir 28. Apparatus 22 could, for example, be made of plastic or Plexiglas, machined or molded. It could be sterilized or provided as a sterile "one use" item.

Housing 26 also includes a slot 32 adjacent back plate 24 and in fluid communication with reservoir 28 for removably receiving an insert 10. An O-ring 34 bears against frame supports 14 when insert 10 is positioned within slot 32 to maintain insert 10 snugly in position. When insert 10 is inserted as shown in FIG. 2, only one side 18 of culture 16 is exposed to reservoir 28. The other side 20 of culture 16 adjacent membrane 12 bears against back plate 24 and is sealed off. In particular, in one embodiment membrane 12 supporting side 20 may be clamped sideways against back plate 24 with a layer of Parafilm sandwiched in between to ensure a complete seal. As will be apparent to a person skilled in the art, other means for temporarily sealing off one side 20 of culture 16 could be envisaged.

In alternative embodiments of the invention, housing 26 could include multiple slots 32. This would permit housing 26 to receive multiple inserts 10 thereby enabling multiple assays to be performed simultaneously.

In accordance with the applicant's invention, each multi-layered cell culture 16 is grown as described above on an insert 10 such that cells proximate at least the exposed sides 18, 20 of culture 16 are actively proliferating. Each insert 10 is then placed within a corresponding slot 32 of apparatus 22 as aforesaid. A test material, such as a drug or other substance, is then inoculated into reservoir 28. The test material is allowed to pass through exposed side 18 and penetrate within culture 16 for a predetermined length of time (which may depend on the test material and the specific type of cell culture employed). Preferably the length of the test period is selected so that cells proximate to the sides 18, 20 of culture 16 remain proliferating throughout. That is, cells proximate to sides 18, 20 are in a similar metabolic state and have similar intrinsic rates of proliferation and sensitivities. Insert 10 is then removed from apparatus 22 and later analyzed, for example immunohistochemically, to determine the extent of penetration of the test drug or other substance. In particular, the invention may be used to identify cells proliferating (or not proliferating) at a location removed from the side 18 of culture 16 which is in fluid contact with the test material.

The invention may be employed as a rapid screening method for assessing drug penetration. This technique differs from multicellular spheroid based cell survival experiments which cannot isolate drug effects from gradients of intrinsic sensitivity.

Figure 3:
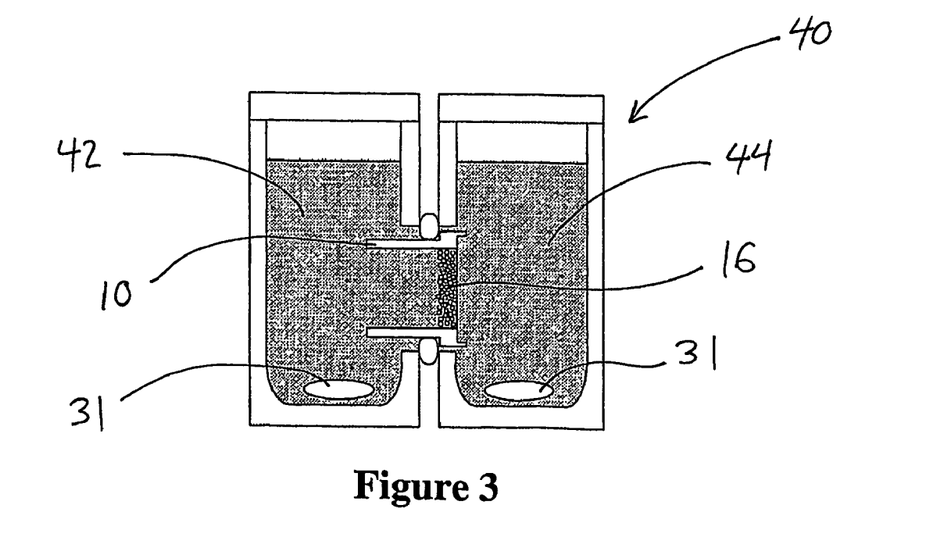
FIG. 3 is a diagrammatic representation of a dual-reservoir apparatus for exposing both sides of a multi-layered cell culture to stirred media.

FIG. 3 illustrates as dual-reservoir apparatus 40 having a first reservoir 42 and a second reservoir 44. As shown in FIG. 3, an insert 10 may be disposed between reservoirs 42, 44 to permit diffusion of media therethrough. Apparatus 40 enables measurement of flux through multi-layered cell cultures 16 and is useful for experimental controls as discussed below. For example, the growth media and oxygenation conditions may be selected in each reservoir 42, 44 to simulate the effect of sealing one side 20 of culture 16 as described above.

EXAMPLES

The following examples will illustrate the invention in further greater detail although it will be appreciated that the invention is not limited to the specific examples.

Example 1

Figure 5:
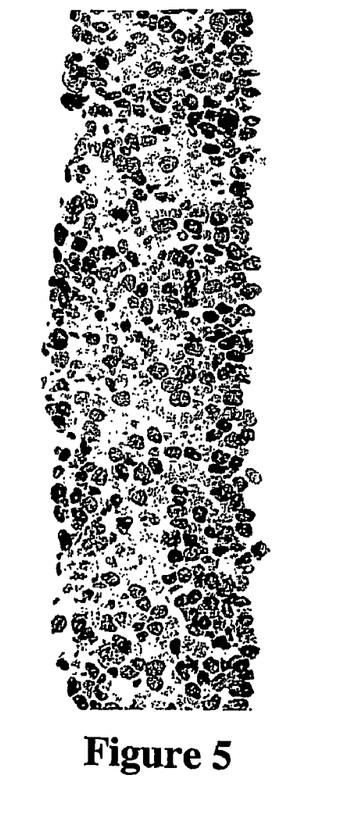
FIG. 5 is a cross-section of a immunohistochemically stained multi-layered cell culture showing the distribution of S-phase cells (darkly stained cells) as a function of position within the culture.
Figure 6:
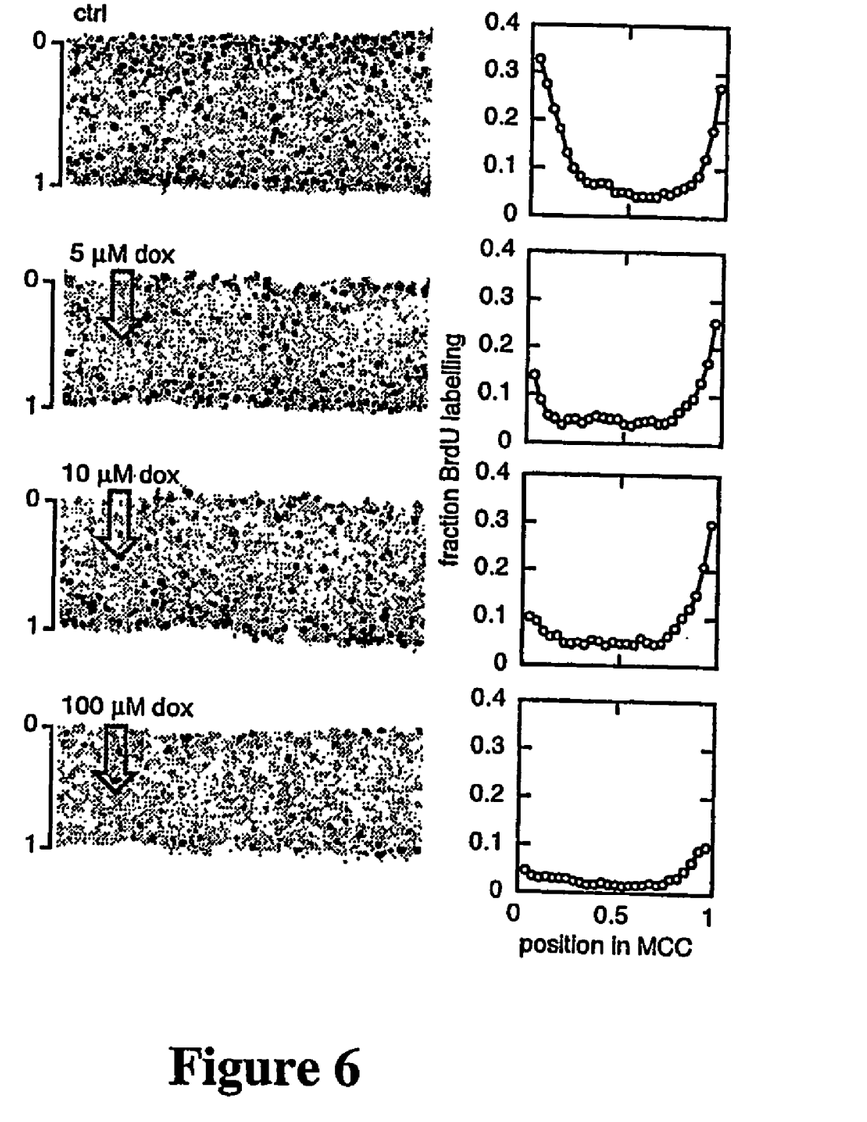
FIG. 6 shows the effect of the anti-cancer agent doxorubicin on proliferation of cells within multi-layered cell cultures having one side sealed off in accordance with the invention. Position within the cultures is scaled between 0 and 1, with 0 being the near (exposed) side and 1 being the far (sealed) side of the MCCs. Concentrations of doxorubicin are 5, 10 and 100 μM as noted in the Figure.

FIGS. 5 and 6 illustrate test results relating to a multi-layered cell culture 16 exposed to the anthracycline doxorubicin (DOX) (i.e. the test material). Cultures 16 were exposed to doxorubicin (at differing concentrations) from one side 18 only for one hour and then incubated for 24 hours in fresh media. Cultures 16 were then exposed to bromodeoxyuridine (BrdUrd) for two hours to label proliferating cells. BrdUrd is a thymidine analogue that is incorporated into DNA during the S phase of the cell cycle and is therefore an effective marker of cellular proliferation. Following BrdUrd exposure, cultures 16 were frozen and cyrosections taken from them. Cryosections were then immunostained to detect BrdUrd labeled S-phase cells. FIG. 6 illustrates the distribution of BrdUrd-labelled cells as a function of position within the cultures. The results clearly indicate that tissue penetration limits doxorubicin effectiveness. In particular, results indicate that at low concentrations doxorubicin only affects cells close to the site of exposure (i.e. exposed side 18) while proliferating cells at the far side of the cultures (i.e. sealed side 20) are only affected at high concentrations.

Example 2

In this example four different anthracyclines clinically used as chemotherapeutic agents were studied, namely doxorubicin (DOX), epirubicin (EPI), daunorubicin (DAU) and the related compound mitoxantrone (MIT). These anthracyclines have a similar mechanism of action but differing physicochemical properties and clinical activities. In addition, the first three agents fluoresce and hence allow for direct comparison of drug effect and drug fluorescence within tissue. The agents are weak bases with pKa values of ~8.3 for DOX, DAU and MIT and ~8.1 for EPI (10, 11) and at pH 7.4 are between 85-90% charged. Entry into cells is believed to occur via passive uptake of the neutral species for all four drugs. Of the three, DAU is most lipophilic, entering cells 3-10 times more quickly than DOX (12, 13), while EPI exhibits an uptake rate approximately twice that of DOX (14). All four drugs bind readily to DNA and accumulate in cells (15). It is believed that the more rapid rate of cellular uptake of DAU may compromise its ability to penetrate into tissue.

MATERIALS & METHODS

Monolayer Culture

HCT-116 human colorectal carcinoma cells were purchased from American Type Culture Collection. Cells were grown in monolayers using minimum essential media (GIBCO/BRL, Burlington, ON, Canada) supplemented with 10% foetal bovine serum (GIBCO/BRL) and passaged every 3-4 days.

Multilayered Cell Culture

Standard tissue culture inserts 10 (CM 12 mm, pore size 0.4 µm, Millipore, Nepean, ON, Canada) were coated with 150 µl collagen (rat tail type I, Sigma), dissolved in 0.01 M HCl and diluted 1:4 with 60% Ethanol to 0.75 mg/ml, and allowed to dry over night. HCT-116, $0.75 \times 10^6$ in 0.5 ml growth media, were then added to the inserts 10 and incubated for 15 hours to allow the cells to attach. The cultures 16 were then incubated for 2 days in custom built growth vessels 21 (FIG. 1(b)) to form multilayered cell cultures (MCCs) 16 which are ~150 µm in thickness. Each growth vessel 21 includes a frame 23 that held the inserts 10 completely immersed in 130 ml of stirred media (700 rpm, 25 mm stir bar) under continual gassing (5% $CO_2$, balance air) at 37° C. The MCCs 16 were grown in batches of 8 cultures of which 6 were treated with drug and 2 were kept as untreated controls.

MCC Penetration Assay

MCCs 16 were exposed to anthracyclines from one exposed side 18 using a polyarcylate apparatus 22 (FIG. 2) designed such that the bottom of each insert 10 is clamped against a flat block 24 of apparatus 22 with a layer of Parafilm (American National Can, Chicago, Ill., USA) sandwiched in between to ensure a complete seal. Each MCC 16 was exposed to a 7.5 ml stirred reservoir 28 kept under controlled gassing and temperature. A silicone O-ring 34 was used to seal the gap between the MCC 16 and the orifice in the reservoir 28. Once placed in the apparatus 22, MCCs 16 were allowed to equilibrate for 45 minutes, drug was then added to the growth medium at concentrations of 0.3, 1, 3 and 10 µM. After 1-hour drug exposure, the reservoirs 28 were rinsed twice with fresh media. MCCs 16 were then incubated for a second hour prior to removal from the apparatus 22 to allow initial drug wash out from the exposed side 18 only. MCCs 16 were then removed, rinsed in fresh media three times for 15 seconds and placed in a growth vessel 21 containing 2 untreated control MCCs 16. Media was replaced at 1 and 4 hours following return to the growth vessel 21, to reduce residual drug levels. Incubation with control MCCs 16 ruled out the possibility that drug wash out into the media from the exposed sides 18 of the MCCs 16 was affecting results. MCCs 16 were left for 1 or 3 days from the time of beginning drug exposure to allow manifestation of drug effect. Following this, 100 µM BrdUrd (5-bromo-2-deoxyuridine, Sigma Chemical, Oakville, ON, Canada) was added to the media and cultures incubated for 4 hours to label S-phase cells. MCCs 16 were then removed, frozen in O.C.T. medium (Tissue-TEK, Torrance, Calif., USA) and stored at −80° C. until sectioning.

MCC Control Assay

Control experiments were carried out using a dual-reservoir apparatus (FIG. 3) in which equal drug exposure was made to both sides 18, 20 of MCCs 16 but under 20% oxygen, 1 g/L glucose in the first reservoir 42 versus 0% oxygen, 0.1 g/L glucose in the second reservoir 44. Media was gassed overnight and then re-equilibrating for 1-hour upon insertion of the MCCs within the dual-reservoir apparatus. For these experiments, the media used was glucose free DMEM GIBCO/BRL, Burlington, ON, Canada) supplemented with 10% foetal bovine serum (GIBCO/BRL). Sodium bicarbonate levels were set to produce pH 7.4 under 5% carbon dioxide. Glucose was then added to the oxygenated side to match physiological levels, 1 g/L. On the anoxic side, the 0.1 g/L glucose was derived from the 10% foetal bovine serum. Drug exposure and wash out were carried out in the manner described in the previous section.

BrdUrd Immunohistochemistry

MCC cryosections (10 µm) were air dried for 24 hours and then fixed in a 1:1 mixture of acetone-methanol for 10 minutes at room temperature. Slides were immediately transferred to distilled water for 10 minutes and then treated with 2 M HCl at room temperature for 1 hour followed by neutralization for 5 minutes in 0.1 M Sodium Borate. Slides were then washed in distilled water and transferred to a PBS (phosphate buffered saline) bath. Subsequent steps were each followed by a 5 minute wash in PBS. BrdUrd incorporated into DNA was detected using a 1:200 dilution of monoclonal mouse anti-BrdUrd (clone BU33, Sigma) followed by 1:100 dilution of anti-mouse peroxidase conjugate antibody (Sigma) and 1:10 dilution of metal enhanced DAB substrate (Pierce, Rockford, Ill.). Slides were then counterstained with haematoxylin, dehydrated and mounted using Permount (Fisher Scientific, Fair Lawn, N.J., USA).

Image Acquisition

The imaging system consisted of a flurouresence microscope (Zeiss III RS, Oberkochen, Germany), a cooled, monochrome CCD video camera (model 4922, Cohu, San Diego, Calif., USA), frame grabber (Scion, Frederick, Md., USA), a custom built motorized x-y stage and customized NIH-Image software (public domain program developed at the U.S. National Institutes of Health) running on a G4 Macintosh computer. The motorized stage allowed for tiling of adjacent microscope fields of view. Using this system, images of MCC sections, 8 mm in length, were captured at a resolution of 1 pixel/µm2. Two cryosections were imaged from each MCC. For MCCs immunostained for BrdUrd incorporation, bright field images were captured. For drug fluorescence visualization, MCCs were imaged using unmounted cryosections 1-hour after sectioning using a 510-555 nm excitation filter and a 575-640 nm emission filter.

Image Analysis

Using the NIH-Image software application and user supplied algorithms, digital images of BrdUrd staining and drug fluorescence within MCC cryosections were analyzed in the following manner. Pixels making up the cryosection were first sorted based on their distance relative to either edge of the tissue. For BrdUrd images, the fraction of positively stained pixels at each position relative to the two edges was then calculated. Pixels two and a half standard deviations above tissue background levels were classified as BrdUrd positive. For fluorescence images, the average value of pixels from each group relative to the two edges was calculated. Detection of tissue edges was facilitated by capturing high-contrast, bright-field images of the MCCs (prior to staining and mounting the slides in the case of the BrdUrd sections).

Results

Effect Based Evaluation of Anthracycline Penetration in MCCs

The penetration of the four anthracyclines was evaluated over a range of concentrations via detection of their effect on S-phase labeling using HCT-116 MCCs grown under controlled conditions in specialized growth vessels, FIG. 1(A). Drug exposures were made to one side of the MCCs using the apparatus shown in FIG. 2; the two sides of the MCCs were defined as the near side 18 (exposed) and far side 20 (sealed off). Exposure from one side enabled a comparison of drug effect on cells that display similar rates of proliferation that are either directly in contact with the drug in media or separated from the drug by the thickness of the culture itself. Following 1 hour drug exposures, cultures were returned to their growth vessels and incubated for 1 to 3 days in fresh media to allow manifestation of drug effect within the tissue.

Figure 7:
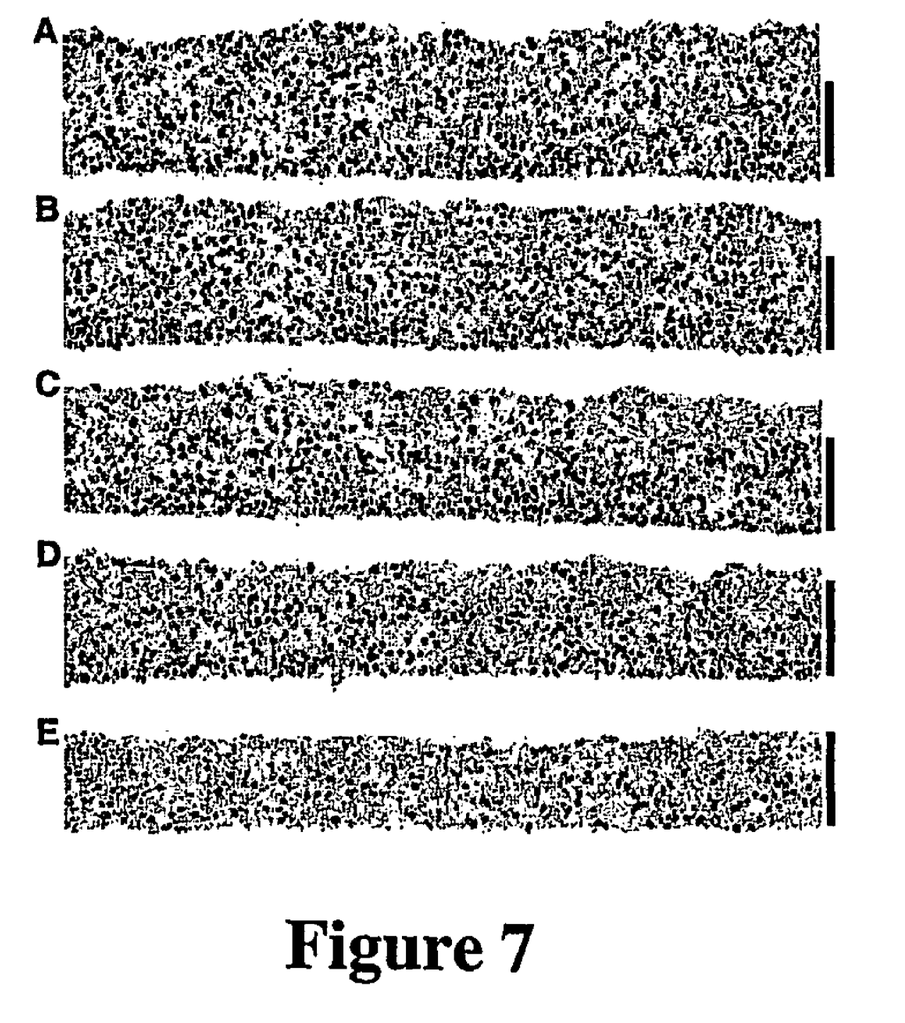
FIG. 7 is a series of microscopic images showing distribution of S-phase cells in multi-layered cell cultures 1 day after a 1-h exposure to EPI from one side (the top surface in each image). (A) untreated, (B) 0.3 (C) 1, (D) 3 and (E) 10 μM EPI. One day following drug exposure cultures were exposed to 100 μM BrdUrd for 4 hours from both sides to label S-phase cells. Cryosections counter stained with haematoxylin. Scale bars, 150 μm, show approximate thickness of culture at time of drug exposure.

Data from experiments where MCCs were exposed for 1 hour to 0.3, 1, 3 and 10 µM EPI and then incubated for 1 day to allow time for manifestation of drug effect are shown in FIG. 7. Results show a gradual increase in depth of the effect of EPI from 0.3 to 10 µM. Only at the 10 µM exposure is EPI found to exert an equal effect to either edge of the MCC. The MCC exposed to 10 µM EPI is approximately the same thickness it was at the time of treatment while the other cultures exposed to lower concentrations have grown increasingly thicker during the day following treatment.

Figure 8:
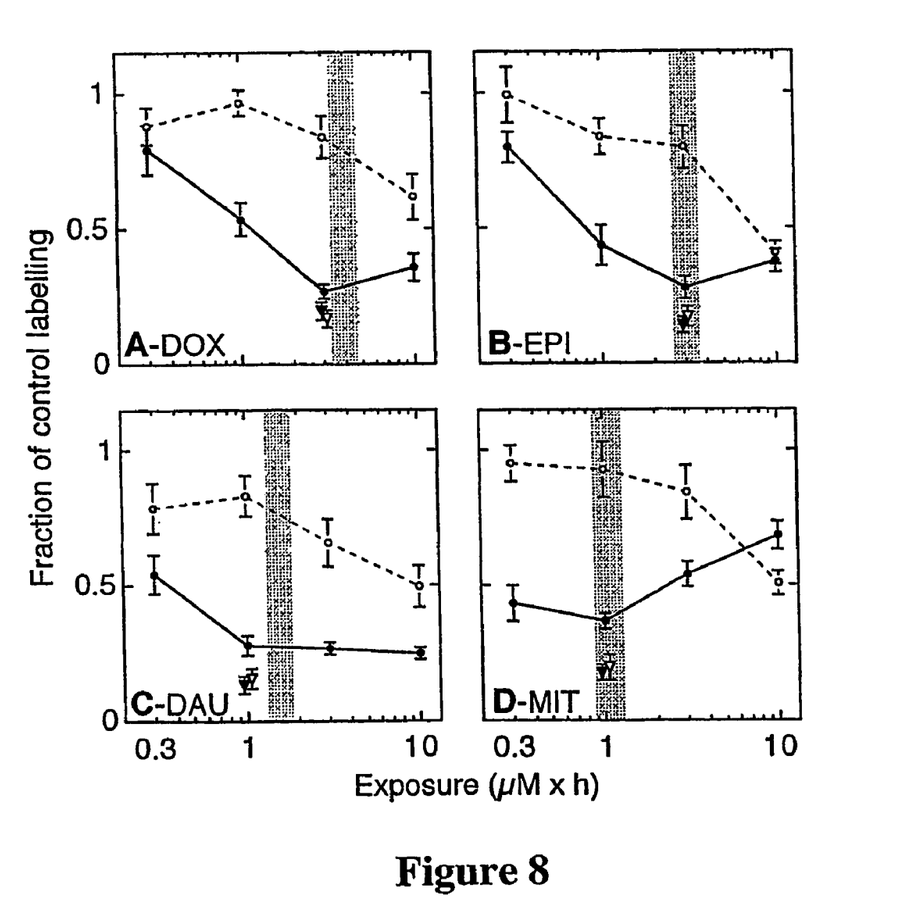
FIG. 8 is a series of graphs comparing the effect of the four test anthracyclines on the first 30 μm of tissue on the near, exposed side (closed circles) and far, sealed side (open circles) of MCCs 1 day after a 1-h exposure using the apparatus shown in FIG. 2; (A) DOX, (B) EPI, (C) DAU and (D) MIT. Control experiments under conditions of normal, (closed triangle), versus low oxygen and glucose, (open tangle), using the dual-reservoir apparatus of FIG. 3 are also shown. Data show BrdUrd immunostaining expressed as the fraction of control levels seen in untreated MCCs from the same experiments. Points show avg±se (n=4-6). Shaded boxes indicate typical clinical exposures.

FIG. 8 shows a summary graph comparing the effect of the four drugs on the near and the far side of MCCs 1 day following a 1-h drug exposure. BrdUrd labeling in the first 30 μm of tissue on either side of the MCCs is expressed as the fraction of labeling seen on the respective sides of untreated MCCs from each experiment. Shaded regions on each panel indicate typical drug exposures achieved in humans (16-19). In all cases the relevant human exposures are not high enough to achieve an equal effect on both sides of the cultures. For DOX, EPI and DAU data from both near and far sides exhibit a general trend of decreasing labeling with increasing drug concentration. However, the MIT data shows an increase in labeling on the near side with increasing drug concentration. Since MIT already exhibits a large effect at the lowest concentration, this is likely due either to non-proliferation related BrdUrd labeling or to cell loss on the near side at the higher concentrations. From the data, estimates of the decrease in drug exposure seen by cells on the far side relative to the near side were ~12-fold for Dox, ~10-fold for EPI, ~30-fold for DAU and greater than 30-fold for MIT. These values were arrived at through determination of the drug concentration which produced an effect on the near side that matched that seen at 10 μM drug on the far side. The average fraction of BrdUrd positive tissue in untreated MCCs was 0.40±0.06 (s.d.) on near side, versus 0.46±0.04 (s.d.) on far sides. This difference is thought to be mainly due to differences in edge detection at the tissue to media transition, near side, in comparison with the more well defined tissue to membrane transition, far side. Middle regions of the MCCs exhibited a significantly lower average BrdUrd stained fraction, 0.28±0.05 (s.d.).

Control experiments were carried out using a dual-reservoir apparatus 40 (FIG. 3) where 1 h drug exposure was made to both sides 18, 20 of MCCs 16 with normal conditions on one side versus low oxygen and glucose on the other. Results are shown in FIG. 8. The low oxygen and glucose levels were chosen to simulate levels seen on the far sealed side 20 of the MCCs 16 during the closed-off experiments. Results were used to estimate what effect an equal drug exposure would have had on the two sides 18, 20 of the MCCs 16 during the closed-off experiments. No significant difference in drug effect between the two sides was observed. These experiments were carried out separately from previous work and performed in different media, which may explain their slightly lower BrdUrd labeling values as compared with the other data presented in FIG. 8.

Figure 9:
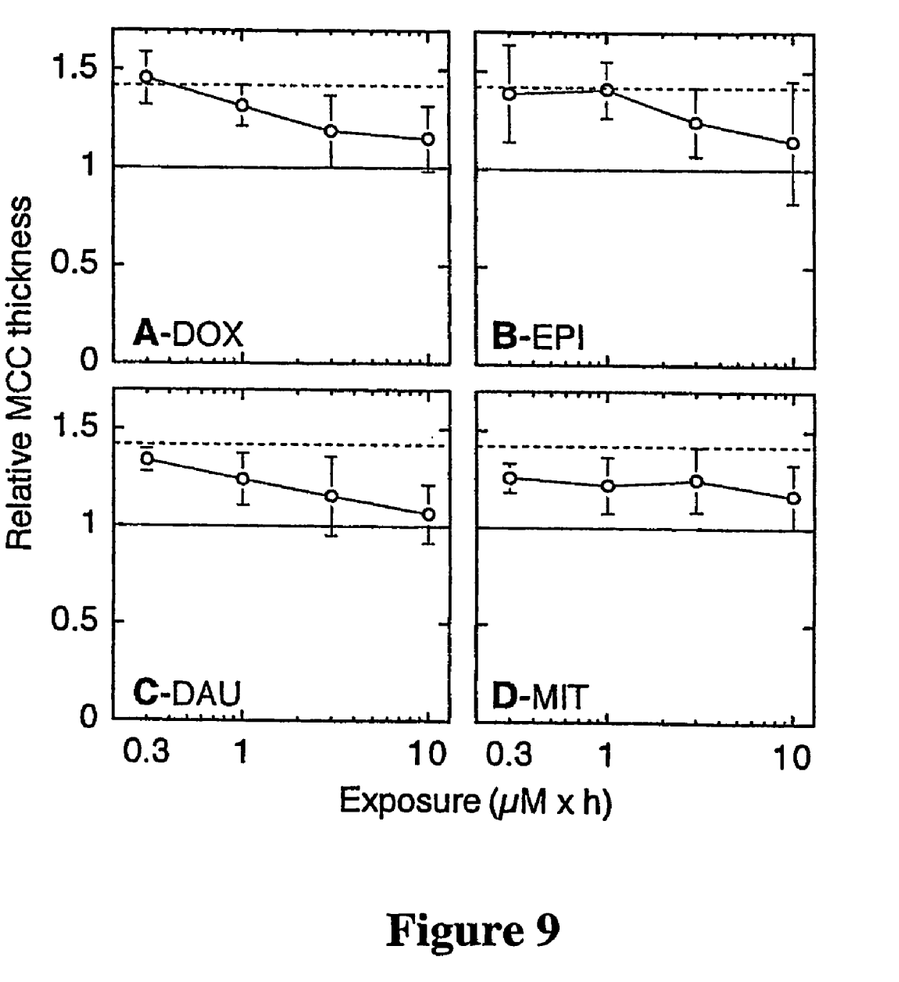
FIG. 9 is a series of graphs showing relative thickness of MCCs 1 day after anthracycline treatment. Cultures were exposed under the same conditions outlined in FIG. 8; (A) DOX, (B) EPI, (C) DAU and (D) MIT. Data is expressed relative to control MCC thickness at time of exposure, 160±20 (sd) μm, as shown by solid horizontal lines. Dashed horizontal lines indicate thickness of untreated MCCs grown along with treated MCCs for 1 day from time of drug exposure. Data points show avg±sd.

The effect of 1 h drug treatment on MCCs 16 thickness 1 day following exposure is summarized in FIG. 9. Data are expressed relative to the average thickness of control MCCs 16 at the time of exposure, 160±20 μm (s.d.), as shown by the solid horizontal lines. Untreated cultures 16 grown for 1 day from time of treatment reached 225±30 μm (s.d.) in thickness, indicated by dashed horizontal lines. Drug treated cultures 16 are seen to lie between their starting thickness and that of untreated cultures left for the additional 24 hours. MCCs 16 exposed at the higher drug concentrations do not grow as thick, as expected from the reduction in cell proliferation. Based on this reduction in proliferation, cell loss due to removal of cells on the near side is likely no more than 2-3 cell layers. In separate experiments, MCCs 16 exposed to 100 μM DOX were only 1-2 cell layers thinner than MCCs 16 exposed to 10 μM DOX, indicating no significant change in cell loss.

Figure 10:
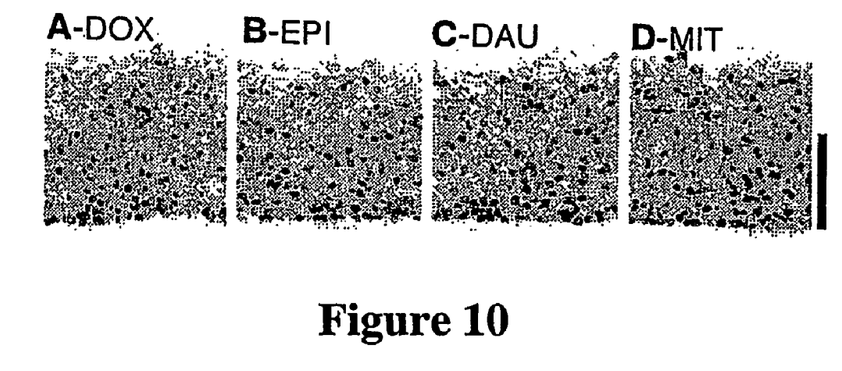
FIG. 10 is a series of microscopic images showing distribution of S-phase cells in MCCs 3 days after exposure from one side (the top surface in each image) to four test anthracyclines at clinically relevant 1 h exposures; (A) 3 μM DOX, (B) 3 μM EPI, (C) 1 μM DAU and (D) 1 μM MIT. Three days after drug exposure cultures were exposed to 100 μM BrdUrd for 4 hours from both sides. Cryosections were counter stained with hematoxylin. Scale bars, 150 μm, show approximate thickness of the cultures at the time of drug exposure.

MCCs 16 cultured for 3 days following clinically relevant exposures showed a similar distribution of S-phase cells as seen after 1 day, FIG. 10, (A) 3 μM×h DOX, (B) 3 μM×h EPI, (C) 1 μM×h DAU and (D) 1 μM×h MIT. Cultures continued to increase in thickness and in all cases there was an increase in proliferation towards the far sides indicating penetration limited drug effectiveness.

Fluorescence Based Evaluation of Anthracycline Penetration in MCCs

Figure 11:
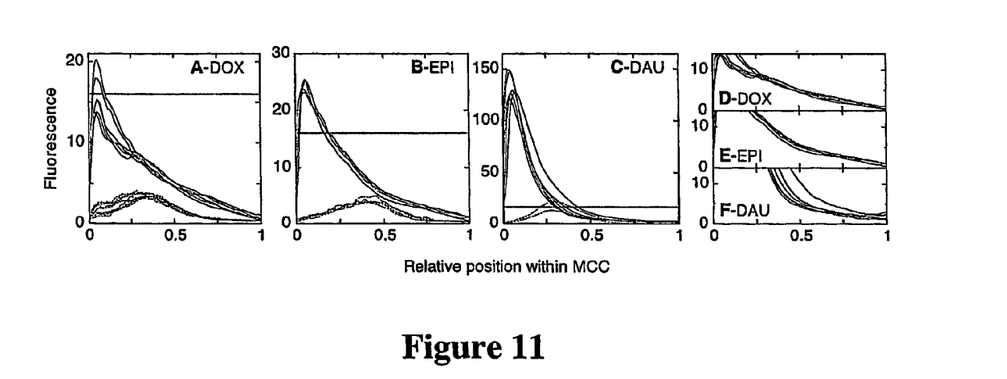
FIG. 11 is a series of graphs showing anthracycline fluorescence in MCCs following a 1-h exposure from one side. Solid lines show data for MCCs frozen immediately after exposure and dashed lines show data for MCCs that were incubated for an additional day in drug free medium; (A)& (D) DOX, (B)&(E) EPI and (C)&(F) DAU. Panels are scaled differently and for reference the dotted horizontal lines in each panel show the averaged peak DOX levels as seen in panel (A). Panels (D)-(F) show data on a magnified scale. Position within the cultures is scaled between 0 and 1, with 0 being the near (exposed) side and 1 being the far (sealed) side of the MCCs. MCCs frozen immediately following exposure measured 140±15 (sd) μm in thickness while MCCs incubated for an additional day were 185±20 (sd) μm in thickness.

The profile of anthracycline derived fluorescence within cultures was examined using the closed-MCC apparatus 22 immediately after the end of a 1-h. 10 mM drug exposure and 1 day following incubation in fresh media. Fluorescence intensity of the drugs in tissue sections serves as a rough indicator of relative drug levels. Only DOX, EPI and DAU, which all posses the same fluorophore, could be examined. Emission intensities of the three drugs in aqueous solution were within 10% of each other. FIG. 11 shows average tissue fluorescence as a function of distance into the cultures from the near sides. Of the three drugs, DOX appears to accumulate the least over the 1-h exposure with EPI and DAU reaching ~1.5 and ~7 times higher levels respectively on the near sides, panels A-C. The much higher accumulation of DAU in the tissue can be related to its higher partition coefficient, leading to a higher rate of entry in cells. Interestingly, the drugs show similar cellular accumulation from the middle regions towards the far sides of each culture, see panels D-F which show the data on the same scale. Position within MCCs 16 is presented as a fraction between 0 and 1 to allow comparison between MCCs 16 taken immediately after drug exposure, which measured 140±15 μm in thickness, and MCCs 16 incubated for the additional day, which were 185±20 μm in thickness.

Figure 12:
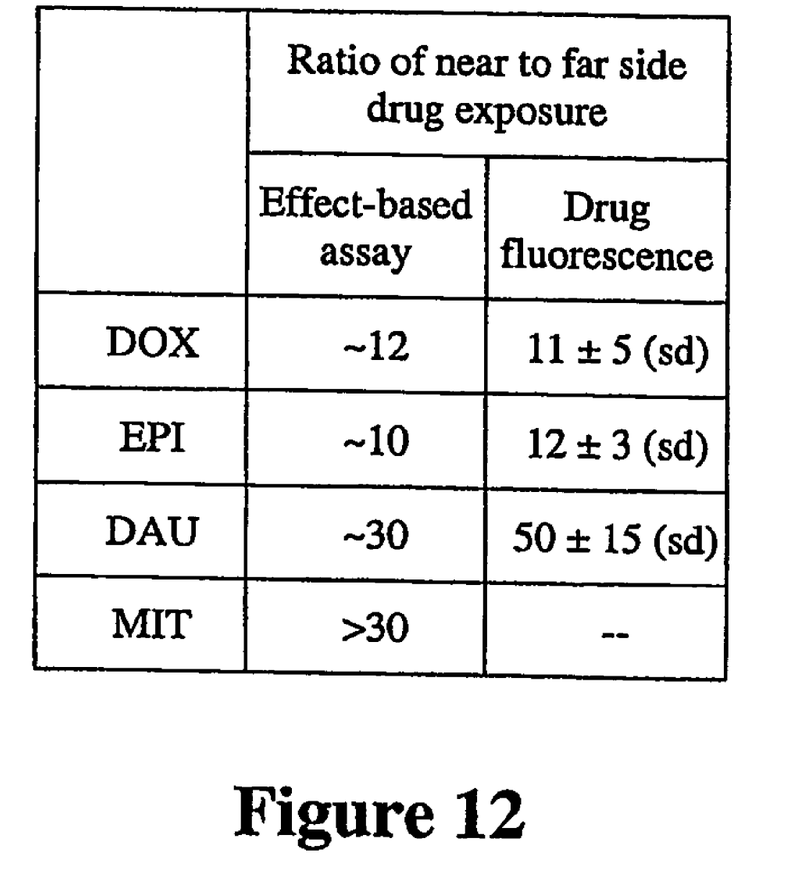
FIG. 12 is a table showing drug exposure to the near (exposed) side relative to the far (sealed) side of MCCs as estimated from the effect-based assay or drug derived fluorescence. Effect-based results are estimated from data shown in FIG. 8. The ratio of fluorescence on each side is calculated from data shown in FIG. 11 using the MCCs frozen immediately following exposure to 10 μM drug over 1 h.

A comparison of effect based evaluation of drug distribution versus drug derived fluorescence is shown in the table of FIG. 12. Results from the two methods indicated that the effect based data reasonably predicts drug distribution as seen from fluorescence data. Effect based results were estimated from data in FIG. 8. The decrease in fluorescence on the far, sealed side 20 relative to the near, exposed side 18, was calculated by averaging fluorescence over the first 30 μm of tissue on each side of the MCCs 16 shown in FIG. 11.

In this Example MCCs 16 were used in accordance with the invention to isolate the role of drug penetration from other factors that determine drug efficacy with depth into tissue. By temporarily closing off one side 20 of the MCCs 16 during drug exposure, a comparison was made between a drug's effect on proliferating cells that were directly exposed to drug and those that lay on the far, sealed side 20 of the MCCs 16. Results showed that limited tissue penetration of the drugs resulted in a 10-30 fold difference in drug exposure between cells on the near, exposed side 18 versus far, sealed side 20 of the cultures.

Fluorescence based detection of the distribution of DOX, EPI and DAU accumulation in MCCs immediately after exposure was consistent with the effect-based assay results for drug penetration. Interestingly, drug fluorescence on the far sides of the cultures was not significantly different for the three drugs. Drug fluorescence following 1 day of wash out was much reduced on the near, exposed side 18 of the cultures but still present towards the central region of the cultures. The relative fluorescence on the exposed side 18 of the MCCs 16 matched the expected ranking of drug uptake rates from cell suspension data, determined mostly by lipophilicity.

A main concern of closing off the MCCs 16 during drug exposure was that deprivation of oxygen and glucose and build-up of lactate on the far (closed-off) side 20 would result in a reduction in cell proliferation and potentially lead to a change in the intrinsic sensitivity of the cells to the drugs. We have previously shown that proliferation continues on the far side 20 of the MCCs during a 1-h exposure preceded by a 45-minute equilibration period (20). In this Experiment, we simulated the effect of oxygen and nutrient deprivation on the far side 20 of the cultures 16 in control experiments (using the dual-reservoir apparatus of FIG. 3) where equal drug exposure was made to both sides 18, 20 of MCCs 16 but with one side under normal oxygen and glucose and the other under low oxygen and glucose. Comparison of drug effect on the two sides 18, 20 were found to be within experimental error for all four drugs.

The distribution of BrdUrd labeling 3 days after 1 h exposures were similar to that seen after 1 day. Due to continued growth of the cultures 16, especially on the far side 20, it was not feasible to perform an in-situ cell survival assay by leaving the cultures for longer periods. However our results are not inconsistent with published work with V79 multicellular spheroids, in which cell survival assays were performed. Following DOX exposure of ~3.5 μM×h, spheroids that were incubated in drug free medium for an additional 24 hours prior to disaggregation exhibited a surviving fraction of ~0.2 on the exposed outer layers versus ~0.6, 130 μm into the tissue (7). In the spheroid study, reduced intrinsic sensitivity of cells in the central area of the spheroids and time of disaggregation were shown to play key roles in determining drug toxicity. In comparison with spheroids, MCCs 16 pose a greater barrier to penetration due to their planar rather than spherical geometry. In contrast, the outward-radial dilution experienced by a drug moving out of a blood vessel and into the surrounding tissue of a tumor likely poses an even greater barrier to penetration.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Rubin, P. and Casarett, G. Microcirculation of tumors— Part I: Anatomy, Function and necrosis. Clin. Radiol., 17: 220-229, 1966.
2. Thomlinson, R. H. and Gray, L. H. The histological structure of some human lung cancers and the possible implications for radiotherapy. Br. J. Cancer, 9: 539-549, 1955.
3. Jain, R. K. Transport of molecules in the tumor interstitium: a review. Cancer Research, 47: 3039-3051, 1987.
4. Jain, R. K. Delivery of molecular and cellular medicine to solid tumors. Adv Drug Deliv Rev, 26: 71-90, 1997.
5. Sutherland, R. M. Cell and environment interactions in tumor microregions: the multicell spheroid model. Science, 240: 177-184, 1988.
6. Minchinton, A. I., Wendt, K. R., Clow, K. A., and Fryer, K. H. Multilayers of cells growing on a permeable support: An in vitro tumour model. Acta Oncologica, 36: 13-16, 1997.
7. Durand, R. E. Slow penetration of anthracyclines into spheroids and tumors: a therapeutic advantage? Cancer Chemother Pharmacol, 26: 198-204, 1990.
8. Kerr, D. J., Wheldon, T. E., Hydns, S., and Kaye, S. B. Cytotoxic drug penetration studies in multicellular tumour spheroids. Xenobiotica, 18: 641-648, 1988.
9. Olive, P. L. and Durand, R. E. Drug and radiation resistance in spheroids: cell contact and kinetics. Cancer Metastasis Rev, 13: 121-138, 1994.
10. Mahoney, B. P., Raghunand, N., Baggett, B., and Gillies, R. J. Tumor acidity, ion trapping and chemotherapeutics. I. Acid pH affects the distribution of chemotherapeutic agents in vitro. Biochem Pharmacol, 66: 1207-1218, 2003.
11. Di Marco, A., Casazza, A. M., Dasdia, T., Necco, A., Pratesi G., Rivolta, P., Velcich, A., Zaccara, A., and Zunino, F. Changes of activity of daunorubicin, adriamycin and stereoisomers following the introduction or removal of hydroxyl groups in the amino sugar moiety. Chem Biol Interact, 19: 291-302, 1977.
12. Demant, E. J. and Friche, E. Kinetics of anthracycline accumulation in multidrug-resistant tumor cells: relationship to drug lipophilicity and serum albumin binding. Biochemical Pharmacology, 56: 1209-1217, 1998.
13. Frezard, F. and Garnier-Suillerot, A. Comparison of the membrane transport of anthracycline derivatives in drug-resistant and drug-sensitive K562 cells. European Journal of Biochemistry, 196: 483-491, 1991.
14. Cantoni, O., Sestili, P., Cattabeni, F., Geroni, C., and Giuliani, F. Comparative effects of doxorubicin and 4'-epidoxorubicin on nucleic acid metabolism and cytotoxicity in a human tumor cell line. Cancer Chemother Pharmacol, 27: 47-51, 1990.
15. Frezard, F. and Garnier-Suillerot, A. Comparison of the binding of anthracycline derivatives to purified DNA and to cell nuclei. Biochimica et Biophysica Acta, 1036: 121-127, 1990.
16. Danesi, R., Innocenti, F., Fogli, S., Gennari, A., Baldini, E., Di Paolo, A., Salvadori, B., Bocci, G., Conte, P. F., and Del Tacca, M. Pharmacokinetics and pharmacodynamics of combination chemotherapy with paclitaxel and epirubicin in breast cancer patients. Br J Clin Pharmacol, 53: 508-518, 2002.
17. Rentsch, K. M., Schwendener, R. A., Pestalozzi, B. C., Sauter, C., Wunderli-Allenspach, H., and Hanseler, E. Pharmacokinetic studies of mitoxantrone and one of its metabolites in serum and urine in patients with advanced breast cancer. Eur J Clin Pharmacol, 54: 83-89, 1998.
18. Pea, F., Russo, D., Michieli, M., Baraldo, M., Ermacora, A., Damiani, D., Baccarani, M., and Furlanut, M. Liposomal daunorubicin plasmatic and renal disposition in patients with acute leukemina. Cancer Chemother Pharmacol, 46: 279-286, 2000.
19. Swenson, C. E., Bolcsak, L. E., Batist, G., Guthrie, T. H., Jr., Tkaczuk, K. H., Boxenbaum, H., Welles, L., Chow, S. C., Bhamra, R., and Chaikin, P. Pharmacokinetics of doxorubicin administered i.v. as Myocet (TLC D-99; liposome-encapsulated doxomibicin citrate) compared with conventional doxorubicin when given in combination with cyclophosphamide in patients with metastatic breast cancer. Anticancer Drugs, 14: 239-25 246, 2003.
20. Kyle, A. H., Huxham, L. A., Baker, J. H., Burston, H. E., and Minchinton, A. I. Tumor distribution of bromodeoxyuridine-labeled cells is strongly dose dependent. Cancer Res, 63: 5707-5711, 2003.

What is claimed is:

1. A method of measuring the penetration of a test substance within a multi-layered cell culture comprising:
    (a) providing a multi-layered cell culture disposed on a permeable support membrane, the cell culture having a first side and a second side;
    (b) maintaining said first side and said second side of said cell culture in contact with a liquid growth medium in a reservoir, wherein cells in said cell culture proximate said first side and said second side are proliferating at similar rates;
    (c) sealing off said second side of said cell culture such that said second side is not in contact with said liquid growth medium for a discrete period of time, wherein said discrete period is selected such that said cells proximate said first side and said second side continue proliferating at similar rates;

(d) exposing said test substance to said first side of said cell culture during said discrete period; and (e) analyzing said cell culture after said discrete period time to determine the degree of penetration of said test substance within said multi-layered cell culture.

2. The method as defined in claim 1, wherein said discrete period is predetermined.

3. The method as defined in claim 1, comprising exposing said first and second sides to growth media after said discrete period of time and before said analyzing.

4. The method as defined in claim 1, wherein said exposing comprises introducing said test substance into said reservoir.

5. The method as defined in claim 1, wherein said analyzing comprises introducing a detector substance into said reservoir for detecting penetration of said test substance.

6. The method as defined in claim 1, wherein said analyzing comprises labeling S-phase cells of said cell culture.

7. The method as defined in claim 1, wherein said analyzing comprises labeling apoptotic cells of said cell culture.

8. The method as defined in claim 1, wherein said analyzing comprises immunohistochemically staining said cell culture.

9. The method as defined in claim 1, wherein said analyzing comprises labeling cells within said cell culture by in situ hybridization.

10. The method as defined in claim 6, wherein said analyzing comprises exposing said cell culture to bromodeoxyuridine.

11. The method as defined in claim 1, wherein said cell culture is substantially planar.

12. The method as defined in claim 1, wherein said cell culture is between approximately 100 to 500 μm in thickness.

13. The method as defined in claim 1, wherein cells comprising said cell culture are tumor cells.

14. The method as defined in claim 1, wherein said test substance is selected from the group consisting of a drug, medicine and cosmetic.

15. The method as defined in claim 14, wherein said drug is a chemotherapeutic agent.

16. The method as defined in claim 1, comprising:
(a) providing a housing defining a reservoir for containing said test substance; and
(b) placing said cell culture into said housing such that only said first side is exposed to said reservoir during said discrete period.

17. A method of identifying substances exhibiting desirable tissue penetration properties comprising carrying out the steps of claim 1.

18. The method as defined in claim 1, wherein said analyzing comprises comparing activity of said test substance on said cells proximate said first and second sides of said cell culture after said discrete period.

19. A method of predicting the penetration of a test substance in living tissue comprising:
(a) providing a multi-layered cell culture disposed on a permeable support membrane, the cell culture having a first side and a second side;
(b) maintaining said first side and said second side of said cell culture in contact with a liquid growth medium, wherein cells in said cell culture proximate said first side and said second side are proliferating at similar rates;
(c) sealing off said second side of said cell culture such that said second side is not in contact with said liquid growth medium for a discrete period of time, wherein said discrete period is selected such that said cells proximate said first side and said second side continue proliferating at similar rates;
(d) exposing said test substance to said first side of said cell culture during said discrete period; and
(e) analyzing said cell culture after said discrete period time to determine the degree of penetration of said test substance within said multi-layered cell culture.

20. The method as defined in claim 19, wherein said analyzing comprises comparing activity of said test substance on said cells proximate said first and second sides of said cell culture after said discrete period.

* * * * *